United States Patent
Böttcher et al.

(10) Patent No.: US 6,617,463 B2
(45) Date of Patent: Sep. 9, 2003

(54) METHOD FOR THE PRODUCTION OF L-ASCORBIC ACID BY LACTONIZATION OF 2-KETO-L-GULONIC ACID OR S2-KETO-L-GULONATE ESTERS

(75) Inventors: Andreas Böttcher, Nussloch (DE); Wolfram Burst, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/275,565

(22) PCT Filed: May 3, 2001

(86) PCT No.: PCT/EP01/04961

§ 371 (c)(1),
(2), (4) Date: Nov. 7, 2002

(87) PCT Pub. No.: WO01/85711

PCT Pub. Date: Nov. 15, 2001

(65) Prior Publication Data

US 2003/0100771 A1 May 29, 2003

(30) Foreign Application Priority Data

May 10, 2000 (DE) .......................................... 100 22 518

(51) Int. Cl.$^7$ ............................................ C07D 305/12
(52) U.S. Cl. ...................................................... 549/315
(58) Field of Search .......................................... 549/315

(56) References Cited

U.S. PATENT DOCUMENTS

| | | | | |
|---|---|---|---|---|
| 2,185,383 A | * | 1/1940 | Pasternack et al. | 549/315 |
| 2,462,251 A | * | 2/1949 | Bassford et al. | 549/315 |
| 5,391,770 A | | 2/1995 | LeFur et al. | 549/315 |
| 5,744,618 A | | 4/1998 | Fechtel et al. | 549/315 |
| 5,744,634 A | | 4/1998 | Veits | 560/174 |

FOREIGN PATENT DOCUMENTS

| | | | |
|---|---|---|---|
| DE | 29 39 052 | | 5/1980 |
| DE | 195 47 073 | | 11/1996 |
| EP | 0 671 405 | | 9/1995 |
| EP | WO 99/03853 | * | 1/1999 |
| EP | WO 99/07691 | * | 2/1999 |
| GB | 601789 | | 5/1948 |
| GB | 1 222 322 | | 2/1971 |
| GB | 2 034 315 | | 6/1980 |
| JP | 48-15931 | | 5/1973 |
| JP | 22 113/75 A | | 7/1975 |
| JP | 58-177986 | | 10/1983 |
| WO | WO 87/00839 | | 2/1987 |
| WO | WO 99/03853 | | 1/1999 |
| WO | WO 99/07691 | | 2/1999 |

OTHER PUBLICATIONS

Francois Popelier "Contribution á Oétude des sulfates acides d'alkyle" Bulletin de la Société Chimique de Belgique vol. 35 No. 7 (1926) pp. 264–276.

Ullmanns Encyclopedia of Industrial Chemistry vol. A27 (1996) pp. 551–557.

Crawford et al. "Synthesis of $_L$–Ascorbic Acid" Advances in Carbohydrate Chemistry and Biochemistry vol. 37 (1980) pp. 79–155.

* cited by examiner

*Primary Examiner*—Amelia Owens
(74) *Attorney, Agent, or Firm*—Keil & Weinkauf

(57) ABSTRACT

The invention relates to a process for the preparation of L-ascorbic acid, in which free 2-keto-L-gulonic acid or $C_3$–$C_{10}$-alkyl 2-keto-L-gulonate is lactonized under acidic conditions in the presence of a water-miscible solvent and where this solvent in situ forms a solvent in which the ascorbic acid formed is poorly soluble.

16 Claims, 1 Drawing Sheet

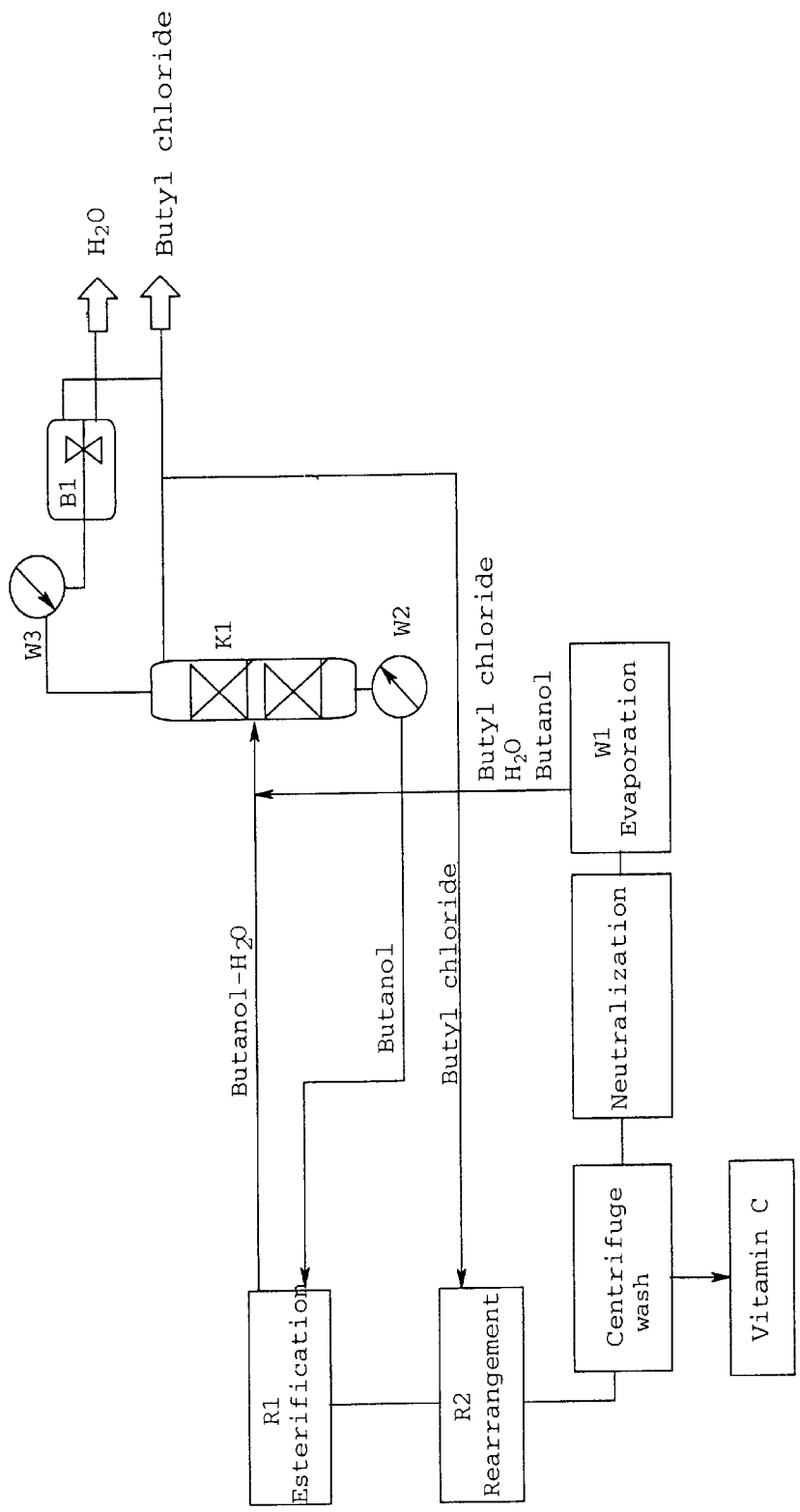
Fig. 1: Lactonization with butyl chloride, H₂O, butanol

METHOD FOR THE PRODUCTION OF L-ASCORBIC ACID BY LACTONIZATION OF 2-KETO-L-GULONIC ACID OR S2-KETO-L-GULONATE ESTERS

This application is a 371 of PCT/EP01/04961 filed May 3, 2001.

The invention relates to a process for the preparation of L-ascorbic acid, in which free 2-keto-L-gulonic acid or $C_3$–$C_{10}$-alkyl 2-keto-L-gulonate is lactonized under acidic conditions in the presence of a water-miscible solvent and where this solvent in situ forms a solvent in which the ascorbic acid formed is poorly soluble.

A large number of process variants for the preparation of L-ascorbic acid have been published in the past. A general survey is found, inter alia, in Crawford et al., Adv. Carbohydrate Chem. 37, 79 (1980) and in Ullmann's Encyclopedia of Industrial Chemistry, Vol. A27, 551–557 (1996).

A number of processes for the preparation of ascorbic acid by reaction of 2-keto-L-gulonic acid with an acid are known.

Thus the reaction of 2-keto-L-gulonic acid with concentrated hydrochloric acid and acetic acid as a solvent is described in U.S. Pat. No. 2,185,383.

JP-AS 58-177986 describes a process which comprises the addition of ethanol and acetone to the sodium salt of 2-keto-L-gulonic acid, neutralization with hydrochloric acid, separation of the precipitated sodium chloride by filtration and subsequently the keeping of the reaction mixture at temperatures in the range from 25° C. to 75° C., whereby L-ascorbic acid is obtained.

The reaction of 2-keto-L-gulonic acid with a mineral acid in an inert solvent in the presence of a surface-active substance is described in JP-B 48-15931.

WO 87/00839 claims a process in which a suspension of 2-keto-L-gulonic acid in an inert organic solvent is reacted in the presence of a surface-active agent with acid catalysis to give L-ascorbic acid.

DE-A-195 47 073 describes a process for the preparation of L-ascorbic acid by reaction of 2-keto-L-gulonic acid with aqueous mineral acid in a solvent mixture comprising an inert organic solvent, an aliphatic ketone and an acid chloride.

WO 99/07691 describes the reaction of 2-keto-L-gulonic acid with concentrated hydrochloric acid at temperatures between 40 and 80° C.

EP-A-0 671 405 discloses a process for the preparation of methyl or ethyl 2-keto-L-gulonate by esterification of 2-keto-L-gulonic acid with methanol or ethanol in the presence of an acidic ion exchanger. It furthermore says in this application that the abovementioned esters can be subjected to an alkaline rearrangement (lactonization) to give ascorbic acid or to give a salt thereof.

U.S. Pat. No. 5,391,770 describes the esterification of 2-keto-L-gulonic acid with subsequent base-catalyzed lactonization of the esters formed to give salts of L-ascorbic acid and liberation of the ascorbic acid by addition of a strong acid.

Japanese Published Patent Specification 22 113/75 describes the esterification of 2-keto-L-gulonic acid with butanol and subsequent acid-catalyzed lactonization in benzene as solvent.

The abovementioned embodiment of the acid-catalyzed rearrangement of 2-keto-L-gulonic acid is economically less attractive on account of its long reaction time and possible secondary reactions of the ascorbic acid formed. Thus as a rule the use of an inert solvent is unavoidable in order to suppress the secondary reactions of the ascorbic acid with aqueous hydrochloric acid. In particular, the complete removal of the catalyst hydrogen chloride necessitates a great technical outlay, which is usually accompanied by the use of a specific solvent. Nevertheless, this procedure is very widely employed industrially. In the acid-catalyzed lactonization of 2-keto-L-gulonic acid, its ester or its isopropylidene-protected form, it is advised to use certain solvents for known reasons. Suitable solvents employed for this batchwise rearrangement in solution advantageously are nonpolar halogenated or nonhalogenated hydrocarbons, such as carbon tetrachloride, chloroform, dichloroethane, 1,2-trichloroethylene, perchloroethylene or aromatic hydrocarbons, such as toluene, chlorobenzene, benzene or xylene. Cyclic carbonates, such as propylene carbonate, can also be used to good effect. These inert solvents lead to working-up problems in the subsequent purification of the reaction product ascorbic acid, as they frequently form azeotropes which are only separable with high expenditure by distillation and can only be completely removed from the valuable product with difficulty by evaporation of stripping. These distillations are associated with loss of product and pollution of the environment. Solvents which are not recovered must additionally be added to the process again in pure form.

A further difficulty is that the 2-keto-L-gulonic acid is always present at the start and in the course of the reaction undissolved in the form of a suspension and a reaction only takes place on the crystal surface. The addition of surface-active substances changes the course of a reaction only a little. What is more, this auxiliary can only be removed from the crude product laboriously and means additional purification steps in order to achieve the desired purity of the L-ascorbic acid. Long reaction times and accordingly large apparatus volumes are furthermore disadvantageous.

The side reactions of the ascorbic acid with the acid catalyst occurring in the acid-catalyzed rearrangement of 2-keto-L-gulonic acid are adequately known. There is therefore no technical process which manages without the use of a technically expensive preliminary purification, e.g. by means of an active carbon purification before the high purification of the ascorbic acid. The service life of this carbon filter is different, depending on the process variant. Usually, however, it lowers the efficiency of the entire process.

Continuous lactonizations of 2-keto-L-gulonic acid and diacetone-2-keto-L-gulonic acid are described in U.S. Pat. No. 2,462,251; DE 29 39052; GB 601789 and GB 1222322. A disadvantage in these processes is that the catalyst recovery, in particular the concentration of the aqueous catalyst solution, is expensive and thus economically disadvantageous.

The continuous lactonization of 2-keto-L-gulonic acid in the presence of aqueous hydrochloric acid at temperatures above 80° C. and addition of lower alcohols after the enolization is described in DE 2939052. By quenching the hot reaction mixture with butanol, rapid cooling and substantial separation of the catalyst as an azeotrope is brought about. The recycling of the hydrochloric acid can only be carried out using a complicated and expensive process concept, as described above.

It is the object of the present invention to make available a process for the preparation of L-ascorbic acid which does not have the abovementioned disadvantages.

We have found that this object is achieved by a process for the preparation of L-ascorbic acid, which comprises lactonizing 2-keto-L-gulonic acid or a melt of $C_3$–$C_6$-alkyl 2-keto-L-gulonate with acid catalysis in the presence exclusively of a solvent or solvent mixture which is miscible with water and in situ forms a solvent in which the ascorbic acid formed is poorly soluble.

In a preferred embodiment, the process according to the invention furthermore comprises the following steps:
  a) esterification of 2-keto-L-gulonic acid or 2,3:4,6-di-O-isopropylidene-2-keto-L-gulonic acid with a $C_3$–$C_6$-alcohol in the presence of an acidic catalyst,
  b) distillation of the excess $C_3$–$C_6$-alcohol together with the water of reaction formed and
  c) lactonization of the $C_3$–$C_6$-alkyl 2-keto-L-gulonate formed with acid catalysis in the presence exclusively of a solvent or solvent mixture which is miscible with water and in situ forms a solvent in which the ascorbic acid formed is poorly soluble.

In the course of the process according to the invention, 2-keto-L-gulonic acid or 2,3:4,6-di-O-isopropylidene-2-keto-L-gulonic acid is first reacted to give the alkyl ester in a single-stage esterification step in the presence of an acidic catalyst. The esterification is carried out in a temperature range from −10 to 160° C., preferably from 20 to 100° C., particularly preferably in a temperature range from 40 to 95° C.

Higher alkyl esters of saturated, branched or unbranched alkyl alcohols having a carbon number of greater than or equal to 3, preferably having an alkyl radical of 3 to 10 carbon atoms, such as n-propanol, isopropanol, 1-butanol, 2-butanol, 2-methyl-1-propanol, 2-methyl-2-propanol, 1-pentanol, 2-pentanol, 3-pentanol, 1-hexanol, 2-hexanol, 1-heptanol, 2-heptanol, 1-octanol, 2-octanol, 3-octanol, 1-nonanol, 2-nonanol, 1-decanol, 2-decanol, 4-decanol, are advantageously suitable for the esterification.

Preferably, alcohols employed for the esterification are those in which L-ascorbic acid is poorly soluble. $C_4$–$C_6$-Alcohols selected from the group consisting of n-propanol, isopropanol, 1-butanol, 2-methyl-1-propanol, 2-methyl-2-propanol, 1-pentanol or 1-hexanol are particularly preferred; 1-butanol and 1-pentanol are very particularly suitable.

The alcohol is employed here in a 2- to 10-fold, preferably 3- to 6-fold, molar excess, based on the 2-keto-L-gulonic acid or 2,3:4,6-di-O-isopropylidene-2-keto-L-gulonic acid employed.

2-Keto-L-gulonic acid is preferably employed as starting material for the synthesis. The acid can in this case be employed either in crystalline form, for example as dried or centrifuge-moist monohydrate or as an anhydrous compound and also as an aqueous solution, for example as a concentrated fermentation solution.

As a rule, the monohydrate of 2-keto-L-gulonic acid is obtained during crystallization from water or water-containing, organic solvents. By centrifuging the crystal slurry, moist monohydrate is obtainable. This can be employed as a centrifuge-moist product directly in the subsequent esterification reaction or dried under mild conditions.

It is also possible to employ a concentrated aqueous solution of the 2-keto-L-gulonic acid directly in the esterification re action. The excess solvent is removed before or during the esterification reaction, e.g. by extraction and phase separation or azeotropic distillation. In particular, this procedure is suitable for a ketogulonic acid solution from a fermentative preparation process. After removal of the biomass by means of standard processes such as filtration, centrifugation or precipitation, the usually colored fermentation solution, preferably after liquid/liquid extraction, can be employed directly without further purification. The excess solvent is then removed as described above, before or during the esterification reaction, e.g. by phase separation or azeotropic distillation.

Anhydrous 2-keto-L-gulonic acid is obtained, inter alia, from the crystalline, optionally centrifuge-moist monohydrate by drying.

Advantageously, the drying or dehydration of the monohydrate of 2-keto-L-gulonic acid can be dispensed with in the process according to the invention, as in the following activation reaction according to the invention an azeotropic dehydration is carried out anyway.

The esterification reaction is catalyzed by addition of a 0.005 to 0.1 molar, preferably a 0.005 to 0.05 molar, amount of an acidic catalyst, in free or polymer-bound form (as strongly acidic cation exchanger) or its ester. The description "acidic cation exchanger" is understood as meaning commercially obtainable resins, such as Lewatit® S 100 and SP 112 (Bayer) or Amberlite® 18 and IRA 120 or Amberlyst® 15 or Duolite® C 20, 26 and C 264 (Rohm & Haas) or Dowex® ion exchangers. Conventional zeolites are also suitable as catalysts.

Further catalysts which are suitable are also organic acids or mineral acids or their derivatives. These include, for example, phosphoric acid, monobutyl phosphates, dibutyl phosphates, monopentyl phosphates, dipentyl phosphates, sulfuric acid, monobutyl sulfates, monopentyl sulfates, hydrogen chloride, p-toluenesulfonic acid, methanesulfonic acid, chlorosulfonic acid, trifluoroacetic acid and other strong, anhydrous acids.

2-Keto-L-gulonic acid, 2,3:4,6-di-O-isopropylidene-2-keto-L-gulonic acid or L-ascorbic acid can also be employed as acidic esterification catalysts.

Preferably, however, sulfuric acid, methanesulfonic acid or monoalkylsulfates of the $C_3$–$C_6$-alcohols used are used; sulfuric acid may be particularly preferably mentioned. The monoalkylsulfates eliminate sulfuric acid at temperatures above 70° C. [Popelier, Bull. Soc. Chim. Belg. 35, 265 (1926)], which acts catalytically. Esterification is therefore usually only possible at relatively high temperatures when using these catalysts.

In order to achieve a conversion which is as complete as possible during the esterification, it is advantageous to remove the water of reaction as completely as possible. Advantageously, in the present process the water of reaction is distilled off with excess alcohol. This is carried out in a pressure range from 20 mbar to normal pressure, preferably in a range from 100 to 800 mbar. The alcohol in this case serves as an entraining agent for the water of reaction formed. Alcohols having less than 3 carbon atoms are therefore not so highly suitable, but possible in principle. The distillate is used for further esterification reactions after removal of the water by phase separation, distillative drying or drying by means of dehydrating agents, such as molecular sieve.

Solvents used for the removal of water from the cycle are advantageously the esterification alcohol or a mixture of this alcohol and a further water-immiscible solvent. Water-immiscible solvents are understood as meaning solvents which dissolve in water at less than 2% by weight. The alcohols to be used according to the invention have only a limited capacity for the exclusion of the water of reaction. In particular in the case of high catalyst acid concentrations or short esterification times, it is advantageous if a second solvent is added as a water-entraining agent even during the esterification reaction. This solvent should form a low-boiling azeotrope with water and optionally be only limitedly miscible with the alcohol in order thus to be able to recycle the alcohol during the esterification reaction after phase separation. Only small amounts, advantageously 10 to 50 mol % based on 2-keto-L-gulonic acid, of this second solvent are needed.

Advantageously, nonpolar halogenated hydrocarbons, e.g. carbon tetrachloride, chloroform, dichloroethane, 1,2-trichloroethylene, perchloroethylene or aromatic hydrocarbons, such as toluene and xylene are employed for this purpose. In addition, propylene carbonate can also be used. A preferred solvent which may be mentioned is perchloroethylene. In a further advantageous procedure, $C_1$–$C_6$-alkyl halides which are derived from alcohols which only have one hydroxy group are used.

In the process according to the invention, the degree of reaction of the 2-keto-L-gulonic acid in the esterification reaction is markedly above 90%, preferably in a range from 95 to 99%.

In the course of the esterification reaction, the 2-keto-L-gulonic acid dissolves, by means of which a good optical indicator of the progress of the reaction is obtained. Depending on the amount of catalyst acid employed, this takes place in a period of a few minutes to a number of hours. Higher temperatures, e.g. in the range from 30 to 150° C., favor the conversion in the case of the esterification reaction. Toward the end of the reaction, if a large part of the excess alcohol has been removed by distillation, the reaction mixture becomes more viscous. Advantageously, the esterification reaction can be considered as terminated if a solvent- and water-free melt of the corresponding alkyl keto-L-gulonate has formed. The viscosity of this melt is dependent on the substance properties of the respective 2-keto-L-gulonate and the temperature.

The reaction mixture solidifies on cooling in a temperature range from 20 to 40° C. On warming, the melt is reformed reversibly and without decomposition. Fresh addition of dry alcohol to complete the esterification reaction, as described, for example, in WO 99-3853, is not necessary under the abovementioned conditions, because a) the esterification reaction takes place almost completely and b) a 100% conversion is not absolutely necessary according to the teaching of the present invention. When using the monohydrate of keto-L-gulonic acid, a higher amount of alcohol is not necessary at the start of the esterification. The esterification rate is determined by the residual water content of the recycled alcohol.

Instead of 2-keto-L-gulonic acid, 2,3:4,6-di-O-isopropylidene-2-keto-L-gulonic acid can also be esterified in the same manner under the abovementioned conditions. In this case, removal of the acetone protective groups additionally takes place. For the removal, two molar equivalents of water are needed, while one mole equivalent of water is simultaneously formed in the esterification reaction. This means that instead of dehydrating agents and physical drying processes chemical reactions for the removal of the water of reaction can also be employed. Most simply, the monohydrate of 2,3:4,6-di-O-isopropylidene-2-keto-L-gulonic acid is therefore employed. The reaction likewise takes place in the pressure and temperature range described above.

The acetone formed is removed by distillation during the esterification reaction at the start or together with excess, water-containing solvent and can be recycled after isolation and obtainment in pure form.

The esterification reaction of 2-keto-L-gulonic acid or 2,3:4,6-di-O-isopropylidene-2-keto-L-gulonic acid can be operated batchwise or continuously. In the continuous esterification, the azeotropic distillation is carried out, for example, in a stirred vessel cascade, a thin-film evaporator or in apparatus operating in a similar manner. Even under these conditions, a molten form of the corresponding alkyl 2-keto-L-gulonate is formed at the end of the esterification. The advantage of this procedure, for example, in comparison to the batchwise esterification is that the reaction time is markedly under an hour with the same conversion and same purity.

In the preferred embodiment of the process according to the invention, according to process steps a) and b) a melt or molten form of the ester is obtained which is highly fluid and can easily be transported in pipelines. This melt can be lactonized directly without isolation or without further purification below 100° C. at normal pressure with acid catalysis in the presence exclusively of a solvent or solvent mixture which is miscible with water and in situ forms a solvent in which the ascorbic acid formed is poorly soluble; in the course of this, the [lacuna] for the activation of the alcohol used is released and the 2-keto-L-gulonic acid is rearranged to L-ascorbic acid in high purity.

Following the esterification reaction of the 2-keto-L-gulonic acid or 2,3:4,6-di-O-isopropylidene-2-keto-L-gulonic acid, the rearrangement (lactonization) of the ester formed—in the form of its melt—to L-ascorbic acid is carried out in process step c) in the presence of an acidic catalyst. Preferably, what is involved here is an anhydrous melt. The lactonization according to the claimed process can also be carried out starting from the free 2-keto-L-gulonic acid or 2,3:4,6-di-O-isopropylidene-2-keto-L-gulonic acid. However, this usually leads to slight losses in yield.

The present invention relates to a lactonization of 2-keto-L-gulonic acid, 2,3:4,6-di-O-isopropylidene-2-keto-L-gulonic acid or its $C_3$–$C_6$-alkyl ester in the absence of an inert solvent, such as nonpolar halogenated hydrocarbons, e.g. carbon tetrachloride, chloroform, dichloroethane, 1,2-trichloroethylene or perchloroethylene or aromatic hydrocarbons, such as toluene, benzene or xylene; but in the presence exclusively of a solvent or solvent mixture which is miscible with water and in situ forms a solvent in which the ascorbic acid formed is poorly soluble. Water-miscible solvents or solvent mixtures are understood as meaning solvents or mixtures thereof which at room temperature (=23° C.) contain at least 5% by weight, advantageously at least 7% by weight, preferably at least 10% by weight, very particularly preferably at least 20% by weight, of water. Poorly soluble for ascorbic acid is understood as meaning a solubility of less than 2 g/l, preferably of less than 1 g/l, in the solvent at room temperature. The solvent or solvent mixture is added at the start of the lactonization reaction and/or is additionally still present from the esterification reaction after incomplete distillation of the solvent. If necessary, more can be added batchwise or continuously during the reaction. A further solvent in which ascorbic acid is only poorly soluble is formed in situ from this solvent or solvent mixture. This further solvent can advantageously be added to the lactonization reaction even from the start of the reaction and can optionally be added batchwise or continuously during the reaction.

Suitable solvents or solvent mixtures are advantageously $C_1$–$C_6$-alcohols which only carry one hydroxy group, or mixtures thereof. Primary, secondary or tertiary alcohols or mixtures thereof can be used; primary or secondary alcohols are preferred. Advantageously, the same higher alcohols according to the invention as are employed for the esterification of the keto-gulonic acids are used. These are, in particular, alcohols with a carbon number of greater than or equal to 3, e.g. n-propanol, isopropanol, n-butanol, isobutanol, tert-butanol, 1-pentanol, 2-pentanol, 3-pentanol, 1-hexanol, 2-hexanol, 1-heptanol or 2-heptanol. Preferably, n-butanol, isobutanol or tert-butanol is used. The pure alcohols of the abovementioned $C_1$–$C_6$-alcohols are particularly preferred, as they can easily be removed. In the presence of, for example, hydrochloric acid or hydrogen chloride, the abovementioned alcohols form the corresponding chloroalkyl halides, in which ascorbic acid is only poorly soluble. These chloroalkyl halides in combination with the starting alcohols make possible an easy and simple purification of the resulting ascorbic acid and can be fed back into the process inexpensively and simply. The monoalkyl halides thus formed in situ in small amounts simplify the purification of the lactonization product ascorbic acid. If necessary, these alkyl halides can be added to the reaction batchwise or continuously before and during the lactonization. Advantageous alkyl halides are $C_1$–$C_6$-alkyl halides selected from the group consisting of ethyl chloride, propyl chloride, butyl chloride, tert-butyl chloride, pentyl chloride or hexyl chloride. Butyl chloride, tert-butyl chloride and pentyl chloride are particularly preferred.

In the process according to the invention, the rearrangement is advantageously carried out using an ester, e.g. using the butyl ester of 2-keto-L-gulonic acid or 2,3:4,6-di-O-isopropylidene-2-keto-L-gulonic acid. The lactonization can also be carried out in the presence of the free acid as described above, however, with slight losses in yield.

When using the butyl ester for the lactonization and introduction of the abovementioned alcohols preferably in the form of butanol, butyl chloride is formed in small amounts from butanol and hydrogen chloride and/or aqueous hydrochloric acid. This influences the lactonization reaction advantageously. In particular, this acts advantageously in the preferred continuous reaction procedure in a tubular reactor, as the solvent additionally formed provides for further reduction of the solubility of the valuable product. It is thus possible to run a higher concentration of the gulonic acid ester, for example of butyl 2-keto-L-gulonate, into the tubular reactor. The space-time yield improves significantly. As an additional advantage, this solvent in addition to high yields and purities which are comparable to or better than the prior art, offers the possibility of a simultaneous simple recycling of the solvent. Slight losses of the solvent in the course of the work-up of the crude product are compensated by the desired reformation of the solvent during the rearrangement reaction. In an advantageous procedure of the process, the losses can be equilibrated via the addition of the appropriate alkyl halides such as the preferred chloroalkyl halides, or else an advantageous higher defined concentration of the alkyl halides can be established in the process.

In comparison with the prior art, according to which the pure alcohol needed for the esterification, for example n-butanol or n-propanol, can only be recovered by a multistage, complex distillation of the inert solvent forming an azeotrope with the alcohol, e.g. perchloroethylene, this means a significant simplification of the process. Thus butyl chloride forms no azeotrope with butanol under the conditions of the solvent work-up.

The lactonization process according to the invention and the preceding esterification can therefore advantageously be carried out continuously. Individual process stages can also be carried out continuously. For example, the lactonization of the butyl ester advantageously takes place in a mixture of n-butanol/butyl chloride/HCl and water in a tubular reactor after rapid heating to reaction temperature.

By the use of the solvents mentioned, the advantageous hydrochloric acid or hydrogen chloride employed as a catalyst can be recycled directly after the reaction by spontaneous depressurization into an evaporator system with some of the solvent or solvent mixture employed. The complicated concentration of the dilute catalyst acid obtained which is customarily necessary before recycling can be completely dropped. The additionally installed ion exchanger, which is generally present, for the neutralization of the mother liquor can also be dropped.

A further advantage of the process according to the invention is that in contrast to the known processes the color-imparting components and other undesired by-products remain in the butanol phase after the extraction of the butanol phase with water and can be purged by simple evaporation as a bottom product.

By means of these measures, in the inventive process removal of the colored and undesirable by-products by means of an active carbon bed can largely be dispensed with.

The continuous lactonization process can advantageously be combined, as described above, with the continuous esterification of the keto-gulonic acids. The alcoholic solutions formed in the process, for example the butanolic solution or melt, can be subjected directly to the continuous lactonization.

2-Keto-L-gulonic acid esters or diacetone-2-keto-L-gulonic acid esters are particularly suitable for the reaction of the process according to the invention. The preparation of the esters is not restricted to the process described above, but serves here only for the illustration of the advantageous procedure. Thus the preparation of the esters is, for example, also realizable in good yields from an aqueous fermentation solution, if appropriate by integration of conventional purification processes (ion exchange, active carbon adsorption or similar processes) by extractive esterification or direct esterification in a reaction column.

The rearrangement (=lactonization) is carried out by the process according to the invention at temperatures above 60° C., advantageously in a temperature range from 70 to 150° C., preferably between 70 and 130° C., particularly preferably between 75 and 110° C. If the process is practiced continuously, the temperature is advantageously to be kept above 90° C. The reaction time is tailored to the appropriate rearrangement temperature in a manner known to the person skilled in the art. The pressure of the reaction is advantageously between 1 and 20 bar, more advantageously between 1 and 15 bar, preferably between 1 and 10 bar, particularly advantageously between 2 and 6 bar. The lactonization can also be carried out at reduced pressure, but this is not useful. The reaction times in the abovementioned temperature range at normal pressure are preferably between 0.25 and 25 hours. Under these conditions, high yields and high purities of the L-ascorbic acid are achieved.

The catalyst acid employed is of crucial importance for the success of the rearrangement reaction. Mineral acids, e.g. phosphoric acid or sulfuric acid, are suitable, but produce low yields of valuable product. Advantageously, hydrochloric acid is employed, either as concentrated aqueous hydrochloric acid or as a gas which is passed directly into the rearrangement mixture. Water is needed for the rearrangement. When using hydrogen chloride, therefore, the necessary amount of water must be added. In the presence of water, too high an acid concentration causes lower yields of valuable product and poorer purities. A concentration of 0.5 to 10%, preferably 0.75 to 7.5%, particularly preferably of 1 to 5%, based on hydrogen chloride gas in the mixture of higher alcohol and solvent indicated above is preferably employed.

The catalyst acid can be present in the rearrangement reactor with the inert solvent, introduced into the solvent as a gas at temperatures up to 50° C. or added to the rearrangement mixture as an aqueous solution.

For longer rearrangement times at relatively low temperatures according to the invention, as a rule the molten form, for example, of the alkyl 2-keto-L-gulonate, preferably the butyl ester, can preferably run into the introduced solvent together with the catalyst acid or inversely. In all cases, adequate mixing of the acid with the reaction mixture is important for the success of the rearrangement. The L-ascorbic acid formed precipitates in crystalline form toward the end of the rearrangement and can be isolated by customary processes, e.g. filtering off with suction, centrifuging off, pressing off or extraction. After washing with the alcohol, which was employed for the esterification, and drying, vitamin C is obtained as a crude product in high purities of at least 95%, preferably at least 97%, particularly preferably at least 98%, very particularly preferably at least 99% chemical purity and good yields of at least 80%, preferably at least 85%, particularly preferably of at least 87%.

The purity and yield of the reaction product can be significantly improved by the advantageous process according to the invention. In the rearrangement, specifically, small amounts of activated carbon are advantageously additionally produced in finely divided form in situ, whereby traces of undesired by-products can be adsorbed and easily separated mechanically. A complicated purification of the resulting L-ascorbic acid is thus superfluous. The proportion of activated carbon is in the range from 0.1 to at most 0.8%. These amounts suffice, for example, to effectively absorb colored impurities which may optionally originate from 2-keto-L-gulonic acid prepared by fermentation. The carbon formed can be conveniently separated off in the course of the isolation of the ascorbic acid.

The yield and purity of vitamin C is influenced by the composition of the solvent mixture in the course of the rearrangement. Too high a water concentration reduces the yield. The water content in this mixture should therefore be in the range from 1 to 10%, preferably in the range from 2 to 7%.

Toward the end of the rearrangement, the rearrangement mixture advantageously contains 50 to 90 percent by weight of the solvent and 50 to 10 percent by weight of the alcohol formed. In this mixture, L-ascorbic acid is poorly soluble and all other starting materials or by-products and the catalyst acid are readily soluble.

The recycling and distillative work-up of the solvent or solvent mixture is advantageously carried out according to the process shown in FIG. 1.

FIG. 1 shows by way of example the esterification of the 2-keto-L-gulonic acid with butanol. The solvent mixture butanol/water formed in the esterification reaction is added to the solvent work-up. The mother liquor obtained in the esterification reaction, containing butyl chloride, butanol and water (if appropriate high-boiling components) is additionally fed into this product stream. The separation of the azeotrope butyl chloride/water can be achieved by a simple two-pressure distillation or by an extractive distillation in the apparatus known according to the prior art. When using other halogenated solvents according to the prior art, e.g. perchloroethylene, the separation of the azeotrope butanol/perchloroethylene would additionally be necessary. This is very laborious.

The esterification product starting from diacetone-2-keto-L-gulonic acid can also be reacted under the same conditions under which the alkyl 2-keto-L-gulonates can be rearranged. The yields and purities are comparable.

The process according to the invention is preferably carried out continuously. Although a number of other acidic catalysts, e.g. mineral acids, are suitable, the reaction is preferably carried out in the presence of the azeotrope-forming catalyst hydrogen chloride even in the rearrangement which is carried out continuously. Its effectiveness can be assisted or increased when the reaction is carried out in the presence of a solid-phase catalyst, e.g. in the presence of a halogen-containing zeolite, as is described in EP 988891. Catalysts of this type are distinguished, inter alia, by high chloride concentrations on the surface and surprisingly long service lives.

In contrast to the batchwise procedure, the continuous reaction is carried out under pressure.

Depending on the starting substance used, the residence time in the tubular reactor is of the order of magnitude of 1 min to 1 hour. When using butyl 2-keto-L-gulonate, residence times in the order of magnitude of 5 to 20 minutes are adequate. The composition of the starting material is important for the residence time and is therefore to be tailored to the specific conditions according to customary criteria by the person skilled in the art. The residence time is selected such that the flow in the reactor approximates a plug flow.

The alcoholic ester solution such as the butanolic butyl ester solution and a mixture of alcohol/alkyl halide/hydrogen chloride/water such as n-butanol/butyl chloride/hydrogen and water are fed to the tubular reactor via a mixer after rapid heating to reaction temperature. Long residence times during the heating phase are to be avoided, as otherwise undesirable secondary reactions can occur. For rapid heating, conventional heat exchangers of high efficiency, induction loops or commercially available microwave flow heaters, e.g. $\mu$WaveFlow 2541 (Püschner) are suitable.

After the end of the reaction, the reaction mixture is depressurized suddenly in an evaporator operating at a normal pressure and some of the solvent is evaporated. Falling-stream evaporators, in particular, are suitable for the depressurization and subsequent evaporation.

A product mixture consisting of n-butanol/butyl chloride/HCl and water is thereby removed from the liquid reaction material discharged and fed to a downstream condenser.

This product mixture is worked up in a customary and very simple manner by condensation at normal pressure. After condensation, the mixture is recycled directly into the rearrangement with the main amount of hydrogen chloride by transport, e.g. with a reciprocating or membrane pump.

In the bottom of the evaporator, a nearly hydrogen chloride-free crude ascorbic acid in alcoholic solution, for example in n-butanol, is obtained.

For prepurification, the reaction material discharged is subjected to an extraction with water. This can be carried out according to the prior art in a continuously operating mixer/settler apparatus or in an extraction column.

The color-imparting components and other undesirable by-products remain in the organic butanol phase. The ascorbic acid thus obtained is found in the almost colorless aqueous phase and has a surprisingly high purity. It is of the order of magnitude of 98.5–99.5%.

After separating off the remaining butanol from the aqueous phase by rectification, the mother liquor is added directly to the crystallization as bottom product.

Advantageous embodiments are described in the Working Examples described below.

EXAMPLES

Working Examples for the Batchwise Procedure

The yields and purities of the experiments described are not optimized and relate to isolated, dried vitamin C. The yield data are based on mol %. The purity of the 2-keto-L-gulonic acid and of the diacetone-2-keto-L-gulonic acid was measured by means of HPLC calibrated against a reference sample. The content of vitamin C was determined in the crude product using the customary iodometric titration method.

Preparation of Butyl 2-Keto-L-gulonate in Butanol

Example 1

The butyl ester employed as a starting material for the batchwise or continuous rearrangement was prepared in a continuously operating esterification column.

The experimental column had a diameter of 30 mm. The column was equipped over a height of 3 m with sheet metal packings. The number of theoretical plates of the column totaled 18 plates. The inlet of the aqueous ketogulonic acid was attached at the 12th theoretical plate (counted from below). The inlet for n-butanol and for the catalytic amount of sulfuric acid was situated at the top of the column.

100 g/h of 50% aqueous 2-keto-L-gulonic acid solution were run in at the 12th theoretical plate at a head pressure of 580 mbar. 173 g/h of n-butanol together with 0.032 mol of sulfuric acid (98% strength) per mole of ketogulonic acid were run in at the top of the column. A bottom temperature of 103° C. was established. The azeotrope water/n-butanol was condensed at the top of the column and led into a separator. The lower aqueous phase was removed and disposed of. The upper organic phase was again added to the top of the column. 63.5 g/h of KGA as a 30% butanolic solution were removed from the bottom of the column. This corresponds to an average yield of 98.8%.

Example 2

The reaction mixture from the continuously operated esterification of 594 g (3 mol) of anhydrous 2-keto-L-gulonic acid and 329 ml (3.6 mol) of n-butanol was treated with 79 g (0.8 mol) of conc. hydrochloric acid in 730 ml (7 mol) of 1-butyl chloride and the mixture was subsequently stirred at 75° C. for 17 hours. The L-ascorbic acid precipitated from the dark reaction mixture was filtered off with suction, washed with n-butanol and dried in vacuo.

Yield: 458 g (86%) of gray crystallizate having a vitamin C purity of 99%.

By means of processes known from the literature, e.g. recrystallization, it was possible to obtain vitamin C of high purity.

Example 3

According to Example 2, instead of anhydrous 2-keto-L-gulonic acid, 2-keto-L-gulonic acid monohydrate was employed. The yield of L-ascorbic acid (crude product) was 85% (purity 98.3%).

Example 4

According to Example 2, instead of anhydrous 2-keto-L-gulonic acid, a 30% strength aqueous 2-keto-L-gulonic acid solution was employed in the esterification reaction. The yield of L-ascorbic acid (crude product) was 85.3% (purity 98.5%).

Example 5

594 g (3 mol) of 2-keto-L-gulonic acid were suspended in a solvent mixture consisting of 730 ml (7 mol) of 1-butyl chloride and 329 ml (3.6 mol) of n-butanol, heated to 73° C. and, after addition of 79 g (0.8 mol) of concentrated hydrochloric acid, the mixture was subsequently stirred for 20 hours. The precipitated, black-gray crystals were filtered off with suction, washed with butanol and dried in vacuo. Yield: 79%. The purity of the product was only 97.5%.

Example 6

Esterification and rearrangement were carried out in analogy to Examples 1 and 2. The difference, however, was that the golden yellow esterification mixture was stirred into butyl chloride/hydrochloric acid. The yield of dried crude product was 89% (purity 99.5%).

Example 7

Esterification and rearrangement were carried out according to Examples 1 and 2. The precipitated L-ascorbic acid was extracted twice with a total of 450 ml of water and purified after clarifying filtration. 87% of L-ascorbic acid having a purity of 99% were found in the aqueous solution after careful evaporation in vacuo.

Example 8

584 g (2 mol) of diactone-2-keto-L-gulonic acid monohydrate were suspended in 667 g (9 mol) of n-butanol and, after addition of 5 g of concentrated sulfuric acid, evacuated to 200 mbar. After heating to 85° C., 580 g of acetone- and water-containing n-butanol were distilled off after 2 hours. The viscous, golden yellow residue was mixed with 730 ml (7 mol) of butyl chloride and rearranged at 72–75° C. for 17 hours after addition of 84 ml of conc. hydrochloric acid. The precipitated L-ascorbic acid was filtered off with suction, washed with n-butanol and dried in vacuo. 580 g (87%) of a pale gray crude product having a purity of 98.9% were obtained.

Working Examples for the Continuous Procedure

The connection with the continuous esterification of keto-L-gulonic acid to KGA butyl ester is described in the following examples.

Example 9

About 1000 g/h of 25% strength butanolic butyl 2-keto-L-gulonate solution were led into the reaction pump via a heat exchanger from the bottom circulation of the esterification column. The recycled solvent mixture n-butanol/butyl chloride/HCl/water was led into the reaction pump via the heat exchanger. The starting temperature after the heat exchanger was adjusted to 120° C. The pressure was 3.9 bar. The temperature was kept at 120° C. in the reaction pump and in the afterreactor.

The reaction mixture was spontaneously depressurized in the evaporator.

The evaporator was operated at normal pressure; an evaporation temperature of 108° C. resulted therefrom. In the condenser, about 1950 g/h having a composition of 82% n-butanol, 3% butyl chloride, 8% [lacuna] were [lacuna] and recycled into the reactor.

In the bottom of the evaporator, about 1050 g/h having a composition of 82% n-butanol, 0.3% butyl chloride, 1000 ppm HCl, 1% water and 16% ascorbic acid were removed. The temperature of the bottom discharge was 108° C. The bottom discharge was led through the condenser and cooled to a temperature of 30° C.

The bottom product of the evaporator was then extracted with water in a 2-stage extraction apparatus. The black butanol phase was separated from the color-imparting components and other by-products in the evaporator. The water-moist distillate was recycled to the esterification column.

The colorless aqueous phase had the following composition:

| | |
|---|---|
| 30% | of ascorbic acid |
| 10% | of n-butanol |
| 60% | of water |
| <0.1% | of HCl |
| <0.1% | of by-products |

The aqueous ascorbic acid solution was freed from the n-butanol in a rectifier column and adjusted to a water content of 20 to 40%.

A simple, two-stage crystallization was sufficient for high purification.

The yield of L-ascorbic acid according to the process variant described was between 92% and 95%, based on the butyl 2-ketogulonate employed. The purity of the crude product was between 98.5 and 99.5%.

According to the prior art, high purification of the L-ascorbic acid can be carried out by means of a downstream crystallization stage.

Example 10

The embodiment corresponded to that of Example 2. The difference, however, was that the tubular reactor was packed with a catalyst according to EP 988891. The reaction conditions remained unchanged.

The yield of isolated crude C was 93.5%. The almost colorless product had a purity of 99%. Coating or loss of activity of the catalyst was not observed even after about 500 cycles.

We claim:

1. A process for the preparation of L-ascorbic acid, which comprises lactonizing 2-keto-L-gulonic acid or a melt of $C_3$–$C_6$-alkyl 2-keto-L-gulonate with acid catalysis in the presence exclusively of a solvent or solvent mixture which is miscible with water and in situ forms a solvent in which the ascorbic acid formed is poorly soluble.

2. A process as claimed in claim 1, wherein the lactonization is carried out with catalysis by a mineral acid.

3. A process as claimed in claim 1, wherein the lactonization is catalyzed by hydrogen chloride or aqueous hydrochloric acid.

4. A process as claimed in claim 1, wherein the lactonization is carried out in the presence of a $C_1$–$C_6$-alcohol as solvent.

5. A process as claimed in claim 3, wherein $C_1$–$C_6$-alkyl halides are formed in situ from the alcohol.

6. A process as claimed in claim 3, wherein an alkyl halide of a $C_1$–$C_6$-alcohol is added to the reaction at the start or during the lactonization.

7. A process as claimed in claim 3, wherein an alkyl halide or a $C_1$–$C_6$-alcohol selected from the group consisting of ethyl chloride, propyl chloride, butyl chloride, tert-butyl chloride, pentyl chloride or hexyl chloride is added at the start or during the lactonization.

8. A process as claimed in claim 1, wherein the lactonization is carried out in a continuous reaction.

9. A process for the preparation of L-ascorbic acid, which comprises the following steps:

a) esterification of 2-keto-L-gulonic acid or 2,3:4,6-di-O-isopropylidene-2-keto-L-gulonic acid with a $C_3$–$C_6$-alcohol in the presence of an acidic catalyst, b) distillation of the excess $C_3$–$C_6$-alcohol together with the water of reaction formed and c) lactonization of the $C_3$–$C_6$-alkyl 2-keto-L-gulonate formed with acid catalysis in the presence exclusively of a solvent or solvent mixture which is miscible with water and in situ forms a solvent in which the ascorbic acid formed is poorly soluble.

10. A process as claimed in claim 9, wherein the esterification in process step a) is carried out using an alcohol selected from the group consisting of n-propanol, isopropanol, 1-butanol, 2-butanol, 2-methyl-1-propanol, 2-methyl-2-propanol, 1-pentanol or 1-hexanol.

11. A process as claimed in claim 9, wherein the esterification in process step a) is carried out in the presence of a mineral acid, of an acidic ion exchanger or of a catalyst attached to a support.

12. A process as claimed in claim 9, wherein the esterification in process step a) is carried out with n-butanol in the presence of sulfuric acid.

13. A process as claimed in claim 9, wherein the reaction temperatures in the process steps a) to c) are in the range from −10 to 160° C.

14. A process as claimed in claim 9, wherein the esterification and lactonization in process steps a) to c) are carried out at pressures in the range from 0.1 to 20 bar.

15. A process as claimed in claim 9, wherein the ester formed in process steps a) and b) is employed directly in lactonization step c) without isolation and purification.

16. A process as claimed in claim 9, wherein process steps a) to c) are carried out continuously.

* * * * *

UNITED STATES PATENT AND TRADEMARK OFFICE
CERTIFICATE OF CORRECTION

PATENT NO.   : 6,617,463 B2
DATED        : September 9, 2003
INVENTOR(S)  : Boettcher et al.

It is certified that error appears in the above-identified patent and that said Letters Patent is hereby corrected as shown below:

<u>Title page,</u>
Item [54], Title, "S2-KETO-L-" should be -- 2-KETO-L --.

Signed and Sealed this

Fourteenth Day of October, 2003

JAMES E. ROGAN
*Director of the United States Patent and Trademark Office*